United States Patent [19]

Robson

[11] Patent Number: 4,879,423

[45] Date of Patent: Nov. 7, 1989

[54] 2-CHLORO-3,6-DIFLUORO-BENZYL HALIDE

[75] Inventor: Michael J. Robson, Bracknell, England

[73] Assignee: Imperial Chemical Industries PLC, London, England

[21] Appl. No.: 230,368

[22] Filed: Aug. 10, 1988

Related U.S. Application Data

[62] Division of Ser. No. 481,948, Apr. 4, 1983, Pat. No. 4,778,822.

[30] Foreign Application Priority Data

May 21, 1982 [GB] United Kingdom ................. 8214906

[51] Int. Cl.$^4$ ............................................. C07L 19/08
[52] U.S. Cl. .................................................... 570/127
[58] Field of Search ......................................... 570/127

[56] References Cited

FOREIGN PATENT DOCUMENTS

87/471 9/1987 Netherlands .

Primary Examiner—Paul J. Killos
Attorney, Agent, or Firm—Cushman, Darby & Cushman

[57] ABSTRACT

The compound 2-chloro-3,6-difluorobenzyl 3-(2-chloro-3,3,3-trifluoroprop-1-en-1-yl)-2,2-dimethylcyclopropane carboxylate in any of its isomeric forms and mixture of these isomeric forms including racemates. Insecticidal compositions containing this compound and methods of using the compound against insect pests are also disclosed.

2 Claims, No Drawings

2-CHLORO-3,6-DIFLUORO-BENZYL HALIDE

This is a division of application Ser. No. 481,948, filed Apr. 4, 1983, now U.S. Pat. No. 4,778,822.

This invention relates to a novel insecticidally active ester.

U.K. patent application No. 2034700A discloses compounds of formula:

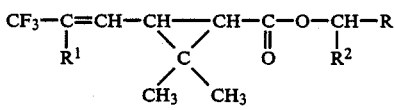

Wherein $R^1$ is trifluoromethyl, fluoro, chloro or bromo, $R^2$ is hydrogen, methyl or cyano, and R is a halophenyl group bearing up to five halogen atoms at least one of which is fluoro. Examples of compounds according to this general formula are disclosed having 1, 2, 4 or 5 halogen atoms in the phenyl ring but no examples of compounds having 3 halogen atoms in the phenyl ring are given. It has now been discovered that a compound having 3 halogen atoms in the phenyl ring is unexpectedly and advantageously more effective than the compounds previously disclosed with 1, 2, 4, or 5 halogen substituents in the control of certain insect pests.

Accordingly the present invention provides the compound 2-chloro-3,6-difluorobenzyl 3-(2-chloro-3,3,3-trifluoroprop-1-en-1-yl)-2,2-dimethylcyclopropane carboxylate having the formula:

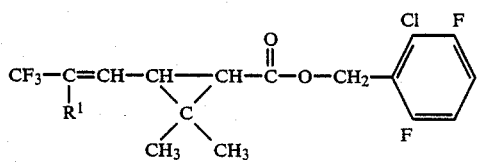

It will be appreciated that the compound can exist in various geometric and optically active isomeric forms and the scope of the invention extends to each isomeric form in isolation as well as mixtures of the isomers including racemates. A particularly useful form of the compound is that derived from the (+/−)-cis form of the cyclopropane acid having the (Z) configuration in the alkenyl group, viz. 2-chloro-3,6-difluorobenzyl (+/−)-cis-3-(Z-2-chloro-3,3,3-trifluoroprop-1-en-1-yl)-2,2-dimethylcyclopropane carboxylate.

The compound of the invention may be prepared by any of the methods disclosed in U.K. patent application no. 2 034 700A. Preferably 3-(2-chloro-3,3,3-trifluoroprop-1-en-1-yl)-2,2 dimethylcyclopropane acid (or the particular isomer or mixture of isomers desired) is reacted with a 2-chloro-3,6-difluorobenzyl halide eg. the bromide.

2-chloro-3,6-difluorobenzyl halides are novel compounds. In a further aspect therefore this invention provides 2-chloro-3,6-difluorobenzyl halides, and their preparation. The bromide, for example, may be prepared by the following scheme from the known compound 2-chloro-6-fluorotoluene.

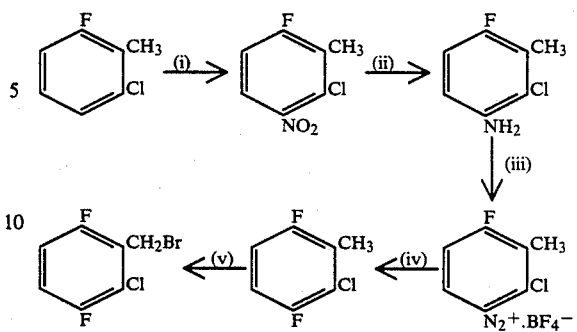

(i) $HNO_3/H_2SO_4$
(ii) $Fe/HCl/H_2O/i\text{-PrOH}$
(iii) 1. $NaNO_2/HCl$ 2. $NaBF_4$
(iv) Heat
(v) $Br_2/CCl_4$ The details of these processes are set forth hereinafter in the Examples.

The compound of this invention may be formulated for use and used as insecticides in the ways indicated for the compounds of U.K. patent application No.2034700A. The compound and its isomeric forms are particularly useful for the control of insect pests which inhabit the soil including Agrotis spp, Agriotis spp and Diabrotica spp. For this purpose they are preferably formulated as granules in which the insecticidally active esters are supported (eg. by coating or impregnation) on mineral, eg. pumice or gypsum, granules, or granules of vegatable matter eg. those derived from corn cobs. They are applied to soil at rates of 0.05 to 25 kg/ha (based on active ingredient), and preferably at rates of 0.1 to 15 kg/ha. Because the invention compound and its isomers have high intrinsic activity against the pests and are also capable of exerting this activity over a prolonged period only one application is required in the course of a growing season to give effective control. The granules may contain from 0.5 to 2.5% by weight of the active ingredient, and the stability of the granules may be improved and the rate of release of the active ingredient may be regulated by the incorporation of a resin or coating with polymeric substance eg. a polyvinyl alcohol based material. The granules may be applied to the surface of the soil adjacent to the furrow in which the plants are growing, and may be lightly incorporated in the soil thereafter, or the granules may be placed in the furrows with the seed at the time of planting.

The invention is illustrated by the following Examples.

EXAMPLE 1

Preparation of 2-chloro-6-fluoro-3-nitrotoluene

To a vigorously stirred mixture of sulphuric acid (136 ml) and nitric acid (134 ml), maintained at 15° C. was added dropwise 2-chloro-6-fluorotoluene (100 g) over a period of 30 minutes. The mixture was alllowed to attain room temperature (20° C.), stirred for 70 minutes, then poured onto crushed ice. Solid 2-chloro-6-fluoro-3-nitrotoluene (70 g) was obtained after filtering and drying.

mp 37°–39°.

N.m.r. ($CDCl_3$) 2.36–2.52(m, 3H); 7.06–7.28 (m, 1H); 7.68–7.88 (m, 1H) p.p.m.

Infra red (liquid paraffin mull) 1355, 1605, 1582 cm$^{-1}$.

EXAMPLE 2

Preparation of 2-chloro-4-fluoro-3-methylaniline

To a mixture of 2-chloro-6-fluoro-3-nitrotoluene (140 g), isopropanol (560 ml) and water (147 ml), hydrogen reduced iron (172.2 g) was added hydrochloric acid (43 drops) and with vigorous stirring the whole heated to reflux temperature (82° C.) for 4 hours. The cooled mixture was then filtered and the filtrate evaporated under reduced pressure giving an oil which on distillation gave 2-chloro-4-fluoro-3-methylaniline (72 g).

b.p. 101°-104°/12 mmHg.

Infra red (thin layer solid evaporated from CHCl$_3$) 1280, 1470, 1640 cm$^{-1}$.

EXAMPLE 3

Preparation of 2-chloro-3,6-difluorotoluene 2-chloro-4-fluoro-3-methylaniline (73 g) was added dropwise, with vigorous stirring to 50% hydrochloric acid (256 ml). The resulting white suspension was cooled to 5° C. and with stirring, sodium nitrite (34.5 g) in water (50 ml), added dropwise. The resultant yellow solution after filtration was cooled to 0° C. and with stirring sodium tetrafluoroborate (71 g) in water (140 ml), added dropwise. The yellow solid formed was filtered off and washed with petroleum ether (6.p 60°-80°) and combined with further similarly washed solid obtained by treating the filtrate, maintained at 0° C., with sodium tetrafluoroborate (71 g) in water (140 ml). The solid was dried overnight over phosphorus pentoxide in vacuo, giving a yield of 98.8 g 2-chloro-4-fluoro-3-methylbenzenediazonium tetrafluoroborate. This was divided into three portions each being placed in a round-bottomed flask (250 ml). The flasks were in turn heated with a naked bunsen flame until decompositio set in and an orange vapor was emitted, which was condensed and collected in a cooled receiver. The orange oil obtained from the three batches was dissolved in diethyl ether (200 ml) and washed with aqueous sodium hydroxide solution (10%, 300 ml) then saturated brine (200 ml). After drying the ethereal solution over anhydrous magnesium sulphate, filtering and evaporating at atmospheric pressure, the residual oil was distilled to give 2-chloro-3,6-difluorotoluene (45 g) b.p. 157°-163°

N.m.r (CDCl$_3$) 2.22-2.35 (m, 3H); 6.86-7.08(m, 2H) p.p.m Infra red (liquid filin) 1230, 1480 cm$^{-1}$.

EXAMPLE 4

Preparation of 2 chloro-3,6-difluorobenzyl bromide

A solution of bromine (24.4 g) in carbon tetrachloride (50 ml) was added slowly over a period of 2 hours 45 minutes to a vigorously stirred solution of 2-chloro-3,6-difluorotoluene (24.4 g) in carbon tetrachloride (150 ml) irradicated by a 200 watt tungsten lamp maintained at 0° C. The solvent was removed by evaporation under reduced pressure and the residual oil distilled to yield 2-chloro-3,6-difluorobenzyl bromide (29.7 g) b.p 96°-101°/0.7 cm Hg.

N.m.r (CDCl$_3$) 4.63-4.74 (m, 2H); 6.95-7.40 (m, 2H) p.p.m

EXAMPLE 5

Preparation of 2-chloro-3,6-difluorobenzyl(+)-cis-3-(Z-2-chloro-3,3,3-trifluoroprop-1-en-1-yl)-2,2-dimethylcyclopropane carboxylate A mixture of (±)-cis-3-(Z-2-chloro-3,3,3-trifluoroprop-1-en-1-yl), -2,2-dimethylcyclopropane carboxylic acid (29.0 g), anhydrous potassium carbonate (250 g), 2-chloro-3,6-difluorobenzyl bromide (29.0 g) and dry acetone (300 ml) was vigorously stirred for 2.5 hours. After filtering, the resultant solution was evaporated under reduced pressure giving an oil which was dissolved in diethyl ether, washed with water and dried over anhydrous magnesium sulphate. The solvent was evaporated and the residual oil purified by distillation giving 2-chloro-3,6-difluorobenzyl (±)-cis-3-(Z-2-chloro-3,3,3-trifluoroprop-1-en-1-yl)-2,2-dimethylcyclopropane carboxylate (35.6 g) b.p. 131°-132° C./0.28 mmHg.

N.m.r (CDCl$_3$) 1/15-1.44 (m, 6H); 1.88-2.33 (m, 2H); 5.24-5.45 (m, 2H); 6.88-7.34 (m, 3H) p.p.m.

Infra red (liquid film): 1140 cm$^{-1}$, 1480 cm$^{-1}$, 1727 cm$^{-1}$.

EXAMPLE 6

This Example illustrates the insecticidal properties of the product of Example 5.

The activity of the product was determined using a variety of insect pects. The product was used in the form of liquid preparations containing 500 parts per million (p.p.m.) by weight of the product. The preparations were made by dissolving the product in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment. Details are given in Table I.

The results of the tests are given in Table I as a grading of mortality on a scale of 0–9 wherein:

0 represents less than 10% mortality
1 represents from 10 to 19% mortality
2 represents from 20 to 29% mortality
3 represents from 30 to 39% mortality
4 represents from 40 to 49% mortality
5 represents from 50 to 59% mortality
6 represents from 60 to 69% mortality
7 represents from 70 to 79% mortality
8 represents from 80 to 89% mortality
9 represents from 90 to 99% mortality

TABLE I

| Pest Species | Support medium/food | Type of test* | Duration (Days) | Grading |
| --- | --- | --- | --- | --- |
| *Musca domestica* (houseflies-adults) | Cotton wool/milk, sugar | contact | 2 | 9 |

TABLE I-continued

| Pest Species | Support medium/food | Type of test* | Duration (Days) | Grading |
|---|---|---|---|---|
| *Aphis fabae* (aphids) | Broad bean leaves | contact | 2 | 9 |
| *Plutella xylostella* (diamond-back moth-larvae) | cabbage leaves | residual | 3 | 9 |
| *Heliothis viriscens* (tobacco budworms) | cotton leaves | residual | 3(6) | 9(9) |
| *Diabrotica balteata* (rootworms) | Filter paper/maize seed | contact | 2 | 9 |
| *Nilaparvata lugens* (plant hoppers) | Rice plants | residual | 3 | 9 |

*"Contact" test indicates that both pests and medium were treated and "residual" indicates that the medium was treated before infestation with the pests.

I claim:
1. 2-chloro-3,6-difluorobenzyl halide.
2. 2-Chloro-3,6-difluorobenzyl bromide.

* * * * *